United States Patent [19]

Venturello et al.

[11] Patent Number: 4,902,803
[45] Date of Patent: Feb. 20, 1990

[54] AROMATIC HETEROCYCLIC PEROXYCARBOXYLIC ACIDS

[75] Inventors: Carlo Venturello, Novara; Claudio Cavallotti, Milan, both of Italy

[73] Assignee: Ausimont S.p.A., Milan, Italy

[21] Appl. No.: 219,141

[22] Filed: Jul. 15, 1988

[30] Foreign Application Priority Data

Jul. 20, 1987 [IT] Italy ................. 21344 A/87

[51] Int. Cl.$^4$ .......................... C07D 213/46
[52] U.S. Cl. ................... 546/318; 546/326; 546/170
[58] Field of Search ................. 546/318, 326

[56] References Cited

FOREIGN PATENT DOCUMENTS 0268907 6/1988 European Pat. Off. .

Primary Examiner—Jane T. Fan
Attorney, Agent, or Firm—Stevens, Davis, Miller & Mosher

[57] ABSTRACT

Nitrogen-containing aromatic heterocyclic (poly)-peroxycarbonxylic acids having the formula:

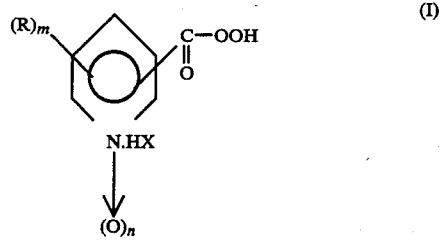

wherein
R represents a hydrogen atom or a straight or branched alkyl, (hetero)cycloalkyl, (hetero)aryl, alkylaryl or arylalkyl group, wherein said groups are optionally substituted, or a carboxylic group or any other substituents non-reactive in the presence of the active oxygen of the peroxycarboxylic group;
n is a number selected from 0 and 1;
m is a number selected from 1, 2 and 3, and
X represents an acidic anion selected from $HSO_4^-$ and $CH_3SO_3^-$, and wherein the pyridinic ring may in its turn be condensed with at least one further (hetero) aromatic or (hetero)cycloalkylic ring;

to their preparation process and to their use as bleaching agents.

9 Claims, No Drawings

AROMATIC HETEROCYCLIC PEROXYCARBOXYLIC ACIDS

DESCRIPTION OF THE INVENTION

The present invention relates to per se new organic (poly)peroxyacids, which can be referred to as aromatic N-heterocyclic (poly)peroxycarboxylic acids, and to the preparation process therefor.

More particularly, the present invention relates to aromatic heterocyclic (poly)peroxycarboxylic acids containing nitrogen in the ring and having the formula (I):

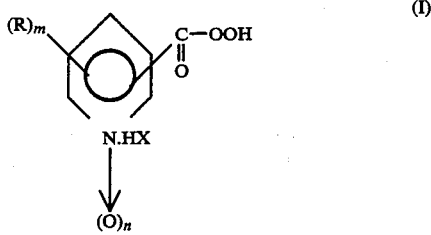

wherein the symbols have the following meanings:

R represents a hydrogen atom or a straight or branched alkyl, (hetero)cycloalkyl, (hetero)aryl, alkylaryl or arylalkyl group, wherein said groups are optionally substituted, a carboxylic group, or other substituents that are nonreactive in the presence of the active oxygen of the peroxycarboxylic group;

n is a number selected from 0 to 1,;

n is a number selected from 1, 2 and 3, and

X represents an acidic anion selected from $HSO_4^-$ and $CH_3SO_3^-$, wherein the pyridinic ring may in turn be condensed with at least one further (hetero)aromatic or (hetero)cycloalkyl ring; to a process for their preparation, and to their use as bleaching agents.

The N-hetero-aromatic peroxycarboxylic compounds having the above formula (I) are per se novel, and constitute a new class products that are highly interesting from an industrial viewpoint. They, in fact, may find a general use, similarly to that already known for peroxyacids, in the field of plastics (as polymerization starters or as oxidizing agents for olefin epoxidation and hydroxylation), and in many other oxidative processes in the field of fine chemistry.

In a more specific way, however, the aromatic N-heterocyclic (poly)peroxycarboxylic acids having the above formula (I) find a particularly efficacious application in the field of bleaching in the detergent industry.

The organic peroxyacids aroused an increasing interest in the industrial field, due, among others, to their excellent possibilities for use as bleaching agents in formulations for medium/low temperature washing, and even more widespread due to energy-saving considerations.

Therefore a large number of literature references exists concerning an, at present, considerable research activity aiming at finding organic peroxyacid compounds endowed with the necessary requisites of bleaching activity, and, in particular, thermal stability and storage stability or shelf life, these latter requisites being essential for the industrial and widespread application of all such compounds.

Therefore, many mono- and di-peroxycarboxylic (aliphatic or carbocyclic) organic peroxyacids are known and used, among others, in the detergent field.

Already described peroxycarboxylic acids are, e.g., diperoxydodecanedioic acid, monoperoxyphthalic acid, diperazelaic acid, substituted diperoxyglutaric and adipic acids, etc.

Applicants are not aware of any previous aromatic N-heterocyclic (poly)peroxycarboxylic acids having the above formula (I), nor of any process for their preparation.

The traditional process contemplates carrying out the oxidation of the substrate (an organic acid, anhydride or ester) with a concentrated solution of hydrogen peroxide, in concentrated $H_2SO_4$ or $CH_3SO_3H$. The strong acidity of this reaction medium and the presence in the substrate of a salifiable nitrogen atom of basic character confer on the said substrate a high solubility in the acidic medium. Such high solubility makes it impossible to apply any of the traditional processes for the isolation of the peroxycarboxylic acid derivative which may be formed in the oxidation reaction with hydrogen peroxide, such as by precipitation or extraction methods with organic solvents.

Surprisingly, in accordance with the present invention, it has been discovered that the nitrogen-containing aromatic heterocyclic (poly)peroxycarboxylic acids having the formula (I), salified on the nitrogen atom with the $HSO_4^-$ or the $CH_3SO_3^-$ anion, may be obtained in a stable form by means of a novel process which is also a part of the present invention.

One object of the present invention is to provide, as per se novel compounds, the nitrogen-containing N-aromatic heterocyclic (poly)peroxycarboxylic acids having the above formula (I).

Another object is to provide a simple and cheap process for the preparation of the above peroxycarboxylic acids having the above formula (I), in a per se stable form.

A further object is the use of aromatic N-heterocyclic peroxycaroboxylic acids having the above formula (I) as bleaching agents in detergent formulations; and especially those destined for low-medium temperature use.

These, and still other objects which will become even clearer for those skilled in the art from the following detailed disclosure, are achieved, according to the present invention, by the nitrogen-containing aromatic N-heterocyclic peroxycarboxylic acids having the above formula (I), and by the relevant preparation process, characterized in that a substrate consisting or consisting essentially of an aromatic N-heterocyclic (poly)carboxylic acid containing a nitrogen atom in the ring, and/or its anhydride and/or its lower alkyl esters, corresponding to the desired peroxycarboxylic acids having formula (I), is reacted with concentrated $H_2O_2$, by operating in a reaction medium selected from concentrated $H_2SO_4$ and $CH_3SO_3H$, and in that the peroxycarboxylic acid (I) is then separated from the reaction mixture by the addition of an organic solvent selected from tetrahydrofuran and ethyl acetate.

In this way the peroxycarboxylic acids having the formula (I) are obtained, generally as stable solids, salified on their nitrogen atom with the $HSO_4^-$ or $CH_3SO_3^-$ anion, and recovered from the reaction medium by means of their insolubilization in the reaction medium by the solvent.

Described in a somewhat different way, the process according to the present invention consists in the peroxycarboxylation reaction of the substrate consisting or consisting essentially of the (poly)acid, anhydride or ester of the aromatic N-heterocyclic carboxylic acid, corresponding to the desired (poly)peroxycarboxylic acid of formula (I), in an acid medium of concentrated $H_2SO_4$ or $CH_3SO_3H$, with $H_2O_2$ and in the subsequent addition, at the end of the reaction, of a suitable organic solvent, which is not miscible with the desired product by dissolving it, and which is capable, on the contrary, of completely dissolving the acid reaction medium (concentrated $H_2SO_4$ or $CH_3SO_3H$), as well as the excess of $H_2O_2$ with the reaction water. This involves the consequent separation, by insolubilization, of the (poly)-peroxycarboxylic acid product having the formula (I), which precipitates, usually, in a stable solid form.

The obtained product is then filtered, washed with the solvent, dried, and so forth, according to per se known techniques.

As said above, the substrate used as the starting material consists or consists essentially of the aromatic N-heterocyclic (poly)carboxylic acid corresponding to the desired (poly)peroxycarboxylic acid of formula (I); it may furthermore be used as its corresponding lower straight or branched $(C_1-C_5)$-alkyl ester or, in case two adjacent carboxy groups (R=COOH) are present, also the corresponding anhydride may be used. These compounds are per se known, and/or can be prepared according to conventional techniques, and/or are available on the market.

Referring to the above formula (I), R is a linear or branched alkyl, (hetero)-aryl, (hetero)-cycloalkyl, alkylaryl or aryl-alkyl group, containing up to 10 carbon atoms, and, in the heterocyclic rings N atoms or O atoms may be present, preferably in the meta- or para-position with respect to the N-heteroatom. Said groups may in turn be substituted with one or more atoms or groups, either equal to or different from one another, inert under the reaction conditions under which the preparation takes place, such as e.g., F, Cl atoms, $NO_2$ groups, lower $C_1-C_5$ alkoxy groups, and so forth.

As an alternative, R may be any other substituent which does not react with the active oxygen of the peroxycarboxylic group, e.g. a carboxylic group, an F atom, a Cl atom, $NO_2$ groups, lower $(C_1-C_5)$-alkoxy groups, and so forth.

Finally, the pyridine ring may be condensed with at least one other (hetero) aromatic or (hetero) cycloalkyl ring, e.g., in the form of a; quinolinic, isoquinolinic, pryidoindolic group, and so forth.

Starting substrates for obtaining the corresponding aromatic N-heterocyclic peroxycarboxylic acids having the formula (I), are, for exemplary purposes: 4-pyridinecarboxylic acid, 2,4-pyridine-dicarboxylic acid, 3-pyridinecarboxylic acid, 2,3-pyridine-dicarboxylic acid and its anhydride, 2,5-pyridine-dicarboxylic acid, 3,5-pyridinedicarboxylic acid, 3-pyridine carboxylic-N-oxide acid, the ethyl ester of 4-pyridine-carboxylic acid, 2,6-dihydroxy-4-pyridine-carboxylic acid, 6-methyl-3-pyridine-carboxylic acid, 2-phenyl-4-quinoline carboxylic acid, 6-isobutyl-3-pyridinecarboxylic acid, 5-p-tolyl-4-pyridine-carboxylic acid, 5-benzyl-3-pyridine-carboxylic acid, 6-fluoromethyl-3-pyridinecarboxylic acid, 2-p-chloro-phenyl-4-quinoline-carboxylic acid, pyrido-indole-4-carboxylic acid, 5-chloro-4-pyridine-carboxylic acid, etc.

In case R=COOH, preferably in a non-ortho-position with respect to the nitrogen atom, the peroxycarboxylation of R may also be carried out, thus obtaining a product of formula (I) with two or more peroxycarboxylic groups.

According to a preferred operating mode, the reaction of peroxycarboxylation of the -aromatic N-heterocyclic carboxylic acids used as the starting substrates, or of their esters or anhydrides, is carried out by gradually adding $H_2O_2$, having a concentration within the range of from approximately 70% to approximately 90% by weight, to a solution of the substrate in concentrated $H_2SO_4$, or in $CH_3SO_3H$, by maintaining the reaction temperature throughout the reaction course within the range of from 15° to 50° C., depending on the reactivity of the substrate.

Otherwise, it has been found advantageous to prepare in advance the salt of the substrate (in the form of an $HSO_4^-$ or $CH_3SO_3^-$ salt), by processing under the same conditions as shown above, but in the absence of $H_2O_2$, and then by separating and peroxidizing the thus-obtained salt to a compound of formula (I).

The amount of $H_2SO_4$ or of $CH_3SO_3H$, determined at a concentration of 100%, is between 5 and 30 moles per mole of substrate, and is preferably between approximately 7 and 10 moles per mole of substrate.

The hydrogen peroxide is used in an amount which is in excess with respect to the substrate, and is between approximately 1.4 and 6 moles per mole of substrate, and preferably between approximately 3 and 4 moles per mole of substrate.

The reaction time depends on the nature of the substrate, on the operating temperature, and on the end total $H_2SO_4/H_2O$ or $CH_3SO_3H/H_2O$ molar ratio present at the end of the reaction. Said ratio is between approximately 2.5 and 10, and preferably between approximately 3 and 7, by approximately adjusting the various concerned parameters.

Reaction times between approximately 30 minutes and 4 hours have been shown to be operative, and generally a reaction time of from approximately 1 hour to approximately 2 hours is sufficient.

The amount of tetrahydrofuran or ethyl acetate solvent used is usually not lower than 4 liters/substrate mole, and furthermore, it is added at a temperature not higher than approximately 10° C.

The aromatic N-heterocyclic peroxycarboxylic acid products having formula (I) are usually solid at room temperature. They may be especially useful in formulations of detergent compositions, e.g., granular formulations, as bleaching agents in solution over a wide temperature range, owing to their good characteristics of storage stability and thermal stability as obtained.

The detergent compositions may be formulated according to the usual pertinent techniques, together with other components and/or additives, etc.

Moreover, the final reaction mixture, before separation of (poly)peroxycarboxylic acid of formula (I), may be subjected to a phlegmatization process.

The present invention is now disclosed in still further detail in the following examples, which are supplied for purely illustrative and not limiting purposes.

The products prepared in the examples were characterized by elemental analysis, by determining their content of active oxygen (by iodometric titration), and by using Fourier Transform Infrared Spectroscopy (FT-IR).

EXAMPLE 1

15 g (0.156 mole) of methanesulphonic acid were charged into a beaker, equipped with stirrer, thermometer, and outer bath.

The internal temperature was increased to 35° C. and 2 g (0.0162 mole) of isonicotinic acid (4-pyridine-carboxylic acid) were added under stirring for 15 minutes.

The above temperature was maintained until a complete dissolution of the carboxylic acid was obtained, and then the temperature was lowered to 15° C. and 3.3 g of $H_2O_2$ at 85% (0.0825 mole) were gradually added so that the temperature was maintained lower than 25° C. The temperature was then increased to 40° C. and the stirring was continued for 2 hours. The reaction mixture was then poured into 200 ml of ethyl acetate maintained under stirring at 10° C. After a few minutes, the products separated in the crystalline form. The stirring was continued for 1 hour at a temperature between 0° and 10° C. and then the solution was filtered under vacuum over a porous septum. The product was directly washed on the filter with ethyl acetate (30 ml), then with ethyl ether (30 ml). The product was then kept inside a $CaCl_2$-drier under vacuum and at room temperature for 1 hour.

3.3 g of crystalline 4-pyridine-peroxycarboxylic acid methanesulphonate were obtained having a purity of 92.4% (active oxygen content 6.3%) corresponding to a yield of 80%.

The product was purified by keeping it under stirring in anhydrous ethanol (35 ml) for 1 hour at room temperature.

Elemental Analysis: Computed for $C_7H_9O_6NS$ : C, 35.74% H: 3.85%; N: 5.95%; O (active): 6.8%; $CH_3SO_3H$, 40.85%. Found: C: 35.80%; H: 3.69%; N: 5.84%; O (active): 6.70%; $CH_3SO_3H$: 40.81%.

Melting Point: 98° C. (with decomposition).

EXAMPLE 2

2.5 g of 2,4-pyridine-dicarboxylic acid were dissolved in 43.3 g (0.45 mole) of methane sulphonic acid. By operating according to the procedures of Example 1, 3.4 g of $H_2O_2$ at 85% (0.085 mole) were added and the stirring was continued at 50° C. for 2 hours. The reaction mixture was then poured into 900 ml of ethyl acetate and, by operating according to Example 1, 3.2 g of crystalline substantially pure 2-pyridine-carboxy-4-peroxycarboxylic acid methanesulphonate were obtained: yield 77%.

Elemental Analysis: Computed for $C_8H_9O_8NS$ : C, 34.40%; H: 3.24%; N: 5.0%; O (active): 0: 5.73%; $CH_3SO_3H$: 34.4%. Found: C: 33.7%; H: 3.17% N: 4.82%; O (active): 5.73% $CH_3SO_3H$: 34.10%.

The product decomposed at 128° C.

EXAMPLE 3

By operating according to the procedures of Example 1, 1.53 g of nicotinic acid (3-pyridinecarboxylic acid) (0.0122 mole) were dissolved into 12 g of $H_2SO_4$ at 96% (0.117 mole) and 2.05 g of $H_2O_2$ at 85% (0.0514 mole) were added, continuing then the stirring at 40° C. for 3½ hours. The reaction mixture was then poured into 300 ml of ethyl acetate according to the procedure of Example 1. By operating as above described, 2.5 g of crystalline 3-pyridine-peroxycarboxylic acid sulphate were separated, having a purity of 87% (active oxygen content of 5.86%; theoretically determined value for ($C_6H_7O_7NS$: 6.74%) and corresponding to a yield of 72%.

Elemental Analysis: Computed for $C_6H_7O_7NS$ : C: 30.39%; H: 2.97%; N: 5.90%; O (active): 6.74%; $H_2SO_4$: 41.36%. Found: C: 30.42%; H: 3.25%; N: 5.98%; O (active): 5.86%; $H_2SO_4$: 41.42%.

Melting Point: 103° C. (with decomposition).

EXAMPLE 4

By operating according to the procedures of Example 1, 4.59 g (0.0365 mole) of nicotinic acid (3-pyridinecarboxylic acid) were dissolved into 36 g (0.375 mole) of methanesulphonic acid and 6 g of $H_2O_2$ at 70% (0.123 mole) were added, continuing then the stirring at 40° C. for 2 ½ hours. The reaction mixture was then poured into 600 ml of tetrahydrofuran according to the procedures of Example 1. By operating as above described, 7.4 g of crystalline 3pyridineperoxycarboxylic acid methanesulphonate were separated, having a purity of 70.5% (active oxygen content of 4.8%—theoretical value 6.8%) and corresponding to a yield of 60%.

The product was purified by keeping it under stirring in anhydrous ethanol (200 ml) for 30 minutes at room temperature.

Elemental Analysis: Computed for $C_7H_9O_6$ NS: C: 35.74%; H: 3.85%;, N: 5.95%; O (active); 6.80%; $CH_3SO_3H$, 40.85%. Found: C: 35.05%; H: 3.77%; N: 5.85%; O (active); 6.75%; $CH_3SO_3H$: 40.79%.

Melting Point: 90° C. (with decomposition).

EXAMPLE 5

By operating according to the procedures of Example 1, 1.49 g (0.01 mole) of the anhydride of 2,3-pyridinedicarboxylic or quinolinic acid were dissolved into 28 g (0.291 moles) of methanesulphonic acid and then 2.3 g of $H_2O_2$ at 85% (0.0575 moles) were added, continuing the stirring at 50° C. for 2 hours. The reaction mixture was then poured into 500 ml of ethyl acetate according to the procedures of Example 1. By operating as above described, 2 g of crystalline, substantially pure 2-pyridine-carboxy-3-peroxycarboxylic acid methanesulphonate were separated yield : 71%.

Elemental Analysis: Computed for $C_8H_9O_8NS$: C: 34.40%; H: 3.24%; N: 5.0%; O (active); 5.73%; $CH_3SO_3H$; 34.4%. Found: C: 34.20%; H: 3.34%;, H: 4.86%; O (active); 5.67%; $CH_3SO_3H$: 34.59%.

The product decomposed at 126° C.

EXAMPLE 6

By operating according to the procedures of Example 1, 1.5 g of quinolinic acid (0.0089 moles) were dissolved in 26 g (0.270 moles) of methanesulphonic acid and then 2.5 g of $H_2O_2$ at 70% (0.0514 moles) were added, continuing then the stirring at 50° C. for 4 hours. The reaction mixture was then poured into 500 ml of ethyl acetate by operating according to the procedures of Example 1. By operating then as in Example 5, 1.8 g of crystalline 2-pyridinecarboxy -3-peroxycarboxylic acid methanesulphonate were separated having a purity at 92% (active oxygen content of 5.27%; theoretical computed value for $C_8H_9O_8$ NS: 5.73%) and corresponding to a yield of 67%.

Elemental Analysis: Computed for $C_8H_9O_8NS$: C: 34.40%; H: 3.24%; N: 4.93%; O (active); 5.72%; $CH_3SO_3H$, 34.40%. Found: C: 34.06%; H: 3.34%; N: 4.86%; O (active) 5.27%; $CH_3SO_3H$: 34.59%.

EXAMPLE 7

By operating according to the procedures of Example 1, 2 g (0.0119 moles) of 2,5-pyridine-dicarboxylic acid were dissolved into 34.6 g (0.360 moles) of methanesulphonic acid and 2.7 g of $H_2O_2$ at 85% (0.0675 moles) were added continuing then the stirring at 47°-48° C. for 2 hours. Continuing according to the procedures of Example 1, the reaction mixture was poured into 800 ml of ethyl acetate and 2.9 g of crystalline substantially pure 2-pyridine-carboxy-5peroxycarboxylic acid methanesulphonate were separated.

Yield: 87%.

Elemental Analysis: Computed for $C_8H_9O_8NS$ : C: 34.40%; H: 3.24%; N: 5.0%; O (active); 5.73%; $CH_3SO_3H$, 34.40%. Found: C: 34.21%; H: 3.28%; N: 4.93%; O (active) 5.72%; $CH_3SO_3H$: 34.70%.

Melting Point: 141° C. (with decomposition).

EXAMPLE 8

By operating according to the procedures of Example 1, 1.5 g (0.00897 moles) of 3.5-pyridinedicarboxylic acid were dissolved into 26 g (0.270 moles) of methanesulphonic acid and 2.05 g of $H_2O_2$ at 85% were added, continuing then the stirring at 35° C. for 2 ½ hours. Continuing the reaction according to the procedures of Example 1, the reaction mixture was poured into 600 ml of ethyl acetate and 2.1 g of a crystalline product having an active oxygen content of 9.09% were separated which, in the form of 3,5-pyridinediperoxycarboxylic acid methanesulphonate, corresponds to a purity of this latter of 83.9%; (theoretical value of the active oxygen computed for $C_8H_9O_9$ NS: 10.84%) and to a yield of 66.0%.

The product decomposed at 87° C..

Elemental Analysis: $C_8H_9O_9$ NS: C: 32.54%; H: 3.07%; N: 4.74%; O (active) 10.84%; $CH_3SO_3H$: 32.5%. Found: C: 32.54%; H: 3.24%; N: 4.74%; O (active); 9.09%; $CH_3SO_3H$: 32.80%.

EXAMPLE 9

By operating according to the procedures of Example 1, 1.4 g (0.028 moles) of nicotinic-N-oxide acid were dissolved into 28 g of sulphuric acid at 96% (0.273 moles) and then 4.8 g of $H_2O_2$ at 85% (0.12 moles) were added, continuing then the stirring at 40° C. for 4 hours. Continuing the reaction according to the procedures of Example 1, the reaction mixture was poured into 700 ml of ethyl acetate and 4.4 g of substantially pure 3-pyridine-peroxycarboxylic - N oxide acid sulphate were separated.

Elemental Analysis: Computed for $C_6H_7O_8NS$: C: 28.46%; H: 2.78%; N: 5.53/%; O (active); 6.32%; $H_2SO_4$: 38.73%. Found: C: 29.06%,; N: 2.91%; N: 5.33%; O (active); 6.31% $H_2SO_4$, 38.60%.

Melting Point: 122° C. (with decomposition).

EXAMPLE 10

2.5 g (0.0165 moles) of ethyl isonicotinate were added under stirring at room temperature to 15 g (0.156 moles) of methanesulphonic acid and then, by operating under conditions such as to not exceed 25° C, 3.3 g of $H_2O_2$ at 85% (0.0825 moles) were added, The reaction was then continued as in Example 1.

1.2 g of crystalline substantially pure 4-pyridine peroxycarboxylic acid methanesulphonate were obtained (active oxygen content 6.73%,; theoretical value 6.80%). Yield: 31%.

The analysis gave the same results as shown in Example 4.

EXAMPLE 11

By operating according to Example 1, 2 g ( 0.0115 moles) of quinoline-4-carboxylic acid were dissolved into 15 g (0.156 moles) of methanesulphonic acid and then 1.5 g of $H_2O_2$ at 85% (0.0375 moles) were added, continuing then the stirring at 40° C. for 2 ½ hours. The reaction mixture was then poured into 200 ml of ethyl acetate, according to the procedures of Example 1. By operating as above described, 2.4 g of crystalline quinoline-4-peroxycarboxylic acid methanesulphonate (yellow crystals) having a purity of 95%, and corresponding to a yield of 72%, were obtained.

Elemental Analysis: Computed for $C_{11}H_{11}O_6$ NS: C: 46.31%; H: 3.88%; N: 4.90%; O (active); 5.60%; $CH_3SO_3H$: 33.68%. Found: C: 46.00%; H: 4.17%; N: 4.35%; O (active); 5.32%; $CH_3SO_3H$, 33.91%.

Melting Point: 102° C. (with decomposition).

EXAMPLE 12

By operating according to the procedures of Example 1, 1.6 g (0.0116 moles) of 6-methyl-nicotinic acid were dissolved into 15 g (0.156 moles) of methanesulphonic acid and then 1.5 g of $H_2O_2$ at 85% (0.0375 moles) were added, continuing then the stirring at 35° C. for 3 hours. The reaction mixture was then poured into 200 ml of ethyl acetate, according to the procedures of Example 1. By operating as described above, 1.4 g of crystalline 6-methyl-3-pyridine-peroxycarboxylic acid methanesulphonate having a purity of 95% (active oxygen content of 6.1%) and corresponding to a yield of 46%, were obtained. The product was purified by keeping it under stirring in anhydrous ethanol (15 ml) for 1 hour at room temperature.

Elemental Analysis: Computed for $C_8H_{11}O_6NS$: C: 38.55 %; H: 4.45%; N: 5.62%; O (active): 6.42%; $CH_3SO_3H$: 38.55%. Found: C: 39.01%; H: 4.66%; N: 5.73%; O (active): 6.42%; $CH_3SO_3H$: 39.00%.

Melting Point: 100° C. (with decomposition).

EXAMPLE 13

(Application Example)

Bleaching tests were carried out with the novel aromatic N-heterocyclic peroxyacid defined as hydrogensulfate of 3-pyridine-peroxycarboxylic acid, as compared to:

(a) H 48 (Mg salt of monoperphthalic acid), a commercial peroxyacid known in the detergent art, and manufactured by INTEROX Chemical Ltd., London, U.K.

(b) Perborate +perborate activator system, which, as known, develops a peroxyacid (peracetic acid) in situ when both products are dissolved in water and which represents the bleaching action at medium-low temperatures ($\leq 60°$ C.) and wherein as the activator, TAED (tetraacetyethylenediamine) was selected, with an amount thereof being used which corresponds to the stoichiometric ratio to the perborate.

(c) sodium perborate ($NaBO_3.4H_2O$) alone.

All tests were carried out at the constant temperature of 60° C., with an initial concentration of total active oxygen in the bleaching equal for all products, and equal to 200 mg/l.

Process

For each test, 500 ml of deionized water, contained in a 1,000 ml flask equipped with a condenser, was heated to a temperature of 60° C. and adjusted to a pH value of 9.5 with a few drops of an NaOH solution; then the bleaching product was added with stirring with such amounts thereof being added as shown in the following Table, and immediately thereafter, two cotton specimens of 10 cm×10 cm stained with standard stains of red wine at EMPA INSTITUTE of St. Gallen (Switzerland), and marked with the "EMPA 114" mark, were added.

The system was subsequently kept stirred for 60 minutes and, at the end of this time, the specimens, rinsed under running water, were dried and ironed, and were then submitted to the evaluation of the bleaching effect by means of measurements of whiteness degree by reflectometry. The results are reported in the following Table 1, wherein the data are expressed as Bleaching %, defined as:

$$\text{Bleaching \%} = \frac{A - B}{C - B} \times 100$$

wherein:

A = degree of whiteness (%) of the specimen bleached during the test;
B = degree of whiteness (%) of the specimen before the test;
C = degree of whiteness (%) of the completely bleached specimen and wherein the degrees of whiteness were measured by means of an Elrepho Zeiss reflectometer, assuming MgO = 100% of whiteness, and using filter N.6 1( $\lambda = 464$ nm).

The data obtained show that the novel peroxyacid of the present invention has a bleaching power higher than the bleaching power of all the other bleaching agents tested.

TABLE 1

| | Amounts used in the test (grams) | Initial concentration of total active oxygen (mg/l) | Bleaching % |
|---|---|---|---|
| 3-pyridine peroxycarboxylic acid hydrogen sulfate (titer = 5.86% of active oxygen) | 1.77 | 200 | 84.5 |
| H 48 (titer = 5.5% of active oxygen) | 1.86 | 200 | 83.0 |

TABLE 1-continued

| | Amounts used in the test (grams) | Initial concentration of total active oxygen (mg/l) | Bleaching % |
|---|---|---|---|
| Perborate tetrahydrate (titer = 10% of active oxygen + TAED (Titer = 93%) | 1.0 0.8 | 200 | 79.9 |
| Perborate tetrahydrate (titer = 10-.0% of active oxygen) | 1.0 | 200 | 68.9 |

What is claimed is:

1. A heterocyclic peroxycarboxylic compound having the formula:

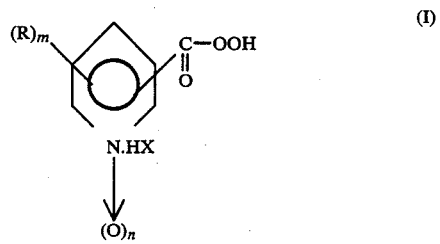

wherein
R is a hydrogen atom or a straight or branched alkyl containing up to 10 carbon atoms, cycloalkyl containing up to 10 carbon atoms, or aryalkyl containing up to 10 carbon atoms; a carboxylic group or a peroxycarboxylic group; and F, Cl, $NO_2$ or an alkoxy-group containing from 1 to 5 carbon atoms;
and wherein:
n is a number selected from O to 1;
m is a number selected from 1, 2 and 3; and
X represents an anion selected from $HSO_4-$ and $CH_3SO_3-$.

2. 4-pyridineperoxycarboxylic acid methanesulphonate.

3. 2-pyridine-carboxy-4-peroxycarboxylic acid methanesulphonate.

4. 3-pyridine-peroxycarboxylic acid sulphate and methanesulphonate.

5. 2-pyridine-carboxy-3-peroxycarboxylic acid methanesulphonate.

6. 2-pyridine-carboxy-5-peroxycarboxylic acid methanesulphonate.

7. 3,5-pyridine-diperoxycarboxylic acid methanesulphonate.

8. 3-pyridine peroxycarboxylic-N-oxide acid sulphate.

9. 6-methyl-3-pyridine-peroxycarboxylic acid methanesulphonate.

* * * * *